(12) United States Patent
Schenck

(10) Patent No.: US 8,851,079 B1
(45) Date of Patent: Oct. 7, 2014

(54) MEDICAL TRAY AND BACKBOARD

(75) Inventor: David Schenck, Erie, PA (US)

(73) Assignee: Trauma Technologies, Inc., Lake City, PA (US)

( * ) Notice: Subject to any disclaimer, the term of this patent is extended or adjusted under 35 U.S.C. 154(b) by 273 days.

(21) Appl. No.: 13/542,377

(22) Filed: Jul. 5, 2012

(51) Int. Cl.
*A61F 5/37* (2006.01)

(52) U.S. Cl.
USPC ............. 128/870; 5/625; 5/626; 5/601

(58) Field of Classification Search
CPC ....... A61F 5/37; A61F 5/3769; A61F 5/3767; A61G 1/00; A61G 1/01; A61G 1/013; A61G 1/04; A61G 1/044; A61G 1/048; A61G 1/06
USPC ........... 128/846, 869, 870; 602/5, 19, 32, 36, 602/39; 5/625–629
See application file for complete search history.

(56) References Cited

U.S. PATENT DOCUMENTS

| | | | | | |
|---|---|---|---|---|---|
| 3,811,139 | A | * | 5/1974 | Shaw | 5/628 |
| 5,560,059 | A | * | 10/1996 | McQueen | 5/625 |
| 6,055,988 | A | * | 5/2000 | Perisho | 128/869 |
| 6,352,460 | B1 | * | 3/2002 | Eiband et al. | 441/80 |
| 6,568,009 | B2 | * | 5/2003 | Linger et al. | 5/627 |
| 6,915,805 | B2 | * | 7/2005 | Crutchfield | 128/870 |
| 2006/0231106 | A1 | * | 10/2006 | Ostrowski | 128/869 |
| 2010/0170036 | A1 | * | 7/2010 | Shirandami | 5/81.1 R |

* cited by examiner

*Primary Examiner* — Patricia Bianco
*Assistant Examiner* — Raymond E Harris
(74) *Attorney, Agent, or Firm* — Richard K Thomson

(57) ABSTRACT

A support tray is equipped with a recess for receiving a medical backboard which has a plurality of medical grade gel pads secured thereto to reduce/eliminate the creation of bed sores. Extender wings can be hooked on the lateral edges of the tray to provide additional surface area for larger patients. Undergirding straps are provided to facilitate transport of the assembly when the wings are being utilized.

8 Claims, 3 Drawing Sheets

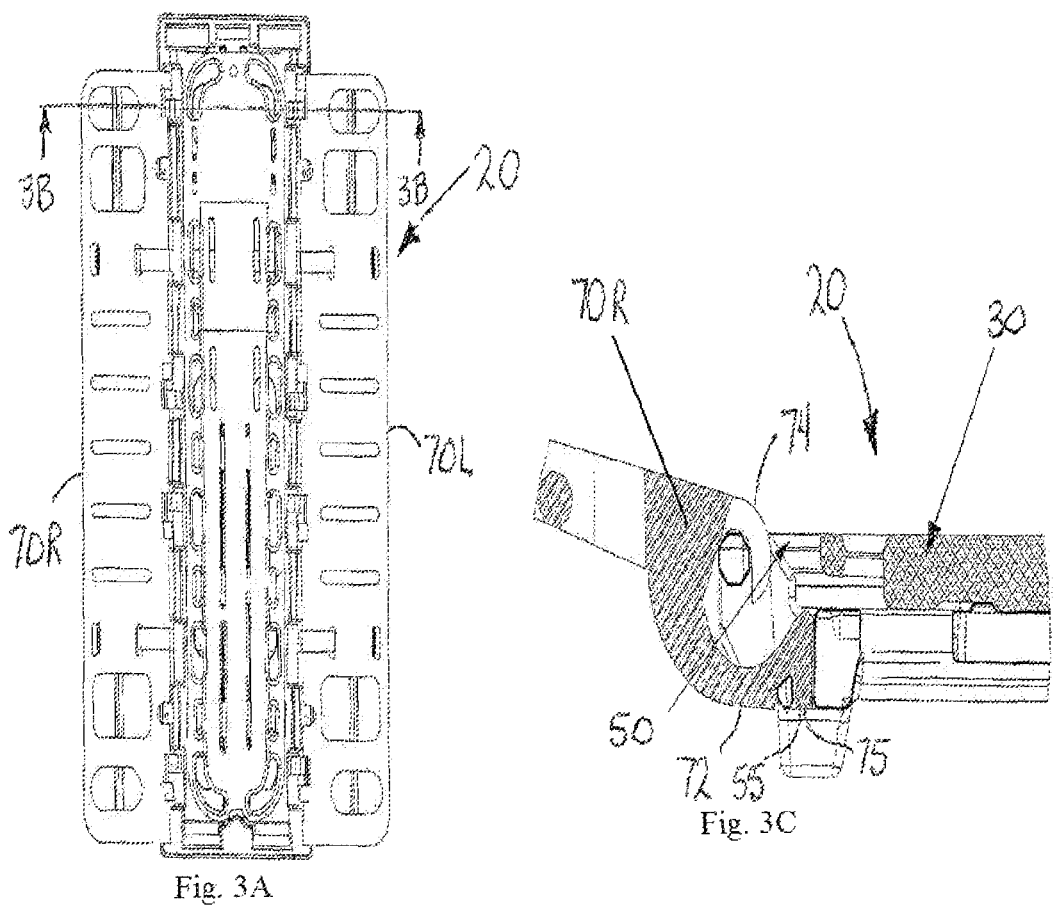
Fig. 3A
Fig. 3C
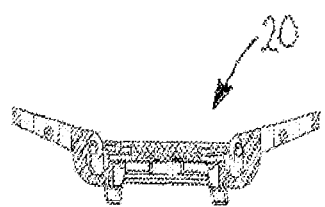
Fig. 3B

MEDICAL TRAY AND BACKBOARD

BACKGROUND AND SUMMARY OF THE INVENTION

The present invention is directed to the field of medical transport. More particularly, the present invention is directed to a medical support tray which receives a medical backboard eliminating the need to move a patient from backboard, to Gurney to x-ray table to MRI table in order to complete diagnosis.

Under the current practice, patients who have been injured, are positioned on a backboard and secured thereto using blocks and tape to immobilize the head; the patient is then transported by ambulance to a hospital. Once there, in order to avoid ulcerations of the skin caused by contact with the rigid backboard, the patient is taken off the backboard and placed on a "Bradford frame", a padded metal frame used to stabilize a patient with pelvic or spinal injuries prior to surgery. Further, if the patient needs x-ray or MRI scans, the metal Bradford frame is inappropriate necessitating one or more additional transfers. It will be appreciated that these moves between support surfaces, prior to fully appreciating the extent of a patient's injury, may well exacerbate her/his injuries in an environment designed to heal, not hurt, the patient. In fact, studies have shown that up to 25% of the post traumatic injuries result from this movement, injuries which can result in paraplegia, quadriplegia, and, in the most extreme cases, death.

It is among the objects of the present invention to provide a tray which can receive a backboard, both the backboard and tray being radiologically transparent eliminating the need to jostle the patient between support surfaces until after the injury has been completely diagnosed. Once extent of the injury is fully known, proper care can be taken to avoid causing additional injury. The backboard is equipped with a plurality of gel pads positioned in three key regions: shoulders, pelvis and heels, to reduce the contact pressure to below 26 mm of Mercury, the pressure which causes venous stasis, or "pressure sores". Further, the medical grade gel selected for this application not only reduces the pressure to a level below venous stasis, it advantageously increases the warming of the soft tissues contacted which enhances blood flow and further reduces the risk of the formation of pressure sores. In addition, the tray has a pair of wings which readily attach to the edges of the primary tray surface to expand the available support for "wide body" patients.

The present invention is directed to a medical support surface upon which a patient will lie for an extended period of time during transport from a trauma site in the medical emergency vehicle, through initial diagnosis and treatment until the patient is ready for her/his recovery bed, the medical support surface including: a) a radiologically transparent rigid backboard defining an area capable of supporting a patient, the backboard having a first pair of lateral edges; b) pressure relief pads attached to the rigid backboard, the pressure relief pads including i) four-way stretch urethane fabric forming an enclosure; ii) medical grade gel within the enclosure; the pressure relief pads reducing a contact pressure between the backboard and a contacted portion of the patient's body to a pressure below that which causes venous stasis whereby the patient may remain on the rigid backboard for the extended period necessary for transport and treatment without causing skin ulcerations; c) a radiologically transparent support tray having a recessed region for receiving the backboard upon which the patient lies. The medical support surface preferably also includes a set of wings attachable to lateral edges of the support tray to expand the area of the support surface beyond the first pair of lateral edges of the backboard. This attachment is effected using attachment means, the attachment means including a plurality of upwardly extending hooks and a plurality of downwardly extending hooks which cooperate to attach to rails extending along each of the second pair of lateral edges. In addition, a plurality of tangs on the wings are received in a plurality of recesses in the support tray to maintain the wings in a fixed longitudinal position relative thereto. The support surface includes a pair of foam comfort pads attached to the second pair of lateral edges of the support tray, the comfort pads being removable to permit attachment of the wings when the wings are needed.

Applicant wishes to thank the Mayo Clinic for its assistance in testing the prototype devices and providing additional assistance in the product development phase of this invention.

Various other features, advantages, and characteristics of the present invention will become apparent after a reading of the following detailed description.

BRIEF DESCRIPTION OF THE DRAWINGS

The preferred embodiment(s) of the present invention is/are described in conjunction with the associated drawings in which like features are indicated with like reference numerals and in which

FIG. 3A is an top view of the first embodiment;

FIG. 3B is a cross-sectional end view taken along line 3B-3B of FIG. 3A; and,

FIG. 3C is a detailed cross-sectional view depicting the attachment means used to secure the extension wings.

DETAILED DESCRIPTION OF THE PREFERRED EMBODIMENT(S)

Figure 1:
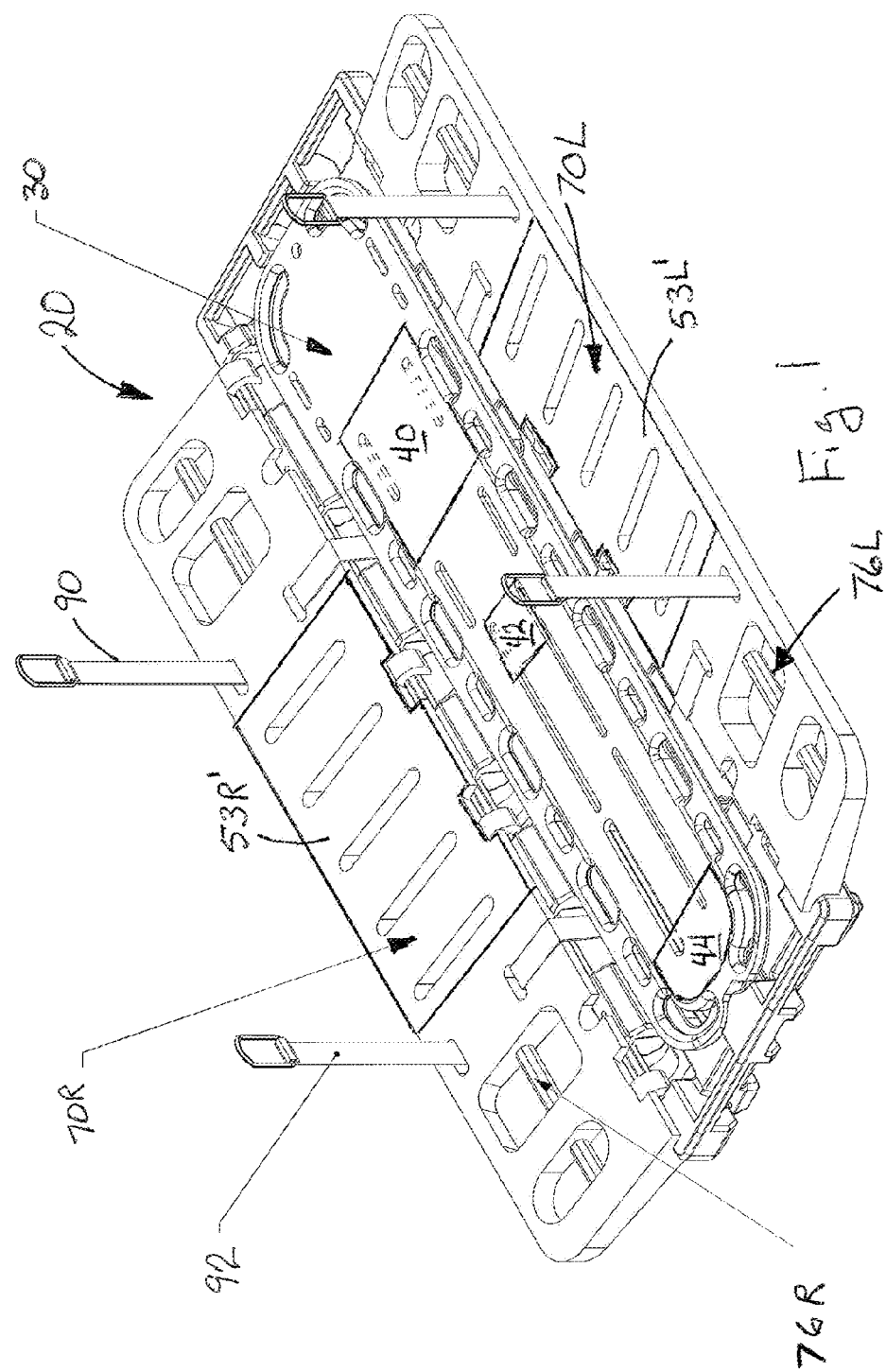
FIG. 1 is a front perspective view of a first embodiment of the medical tray and backboard of the present invention.
Figure 2:
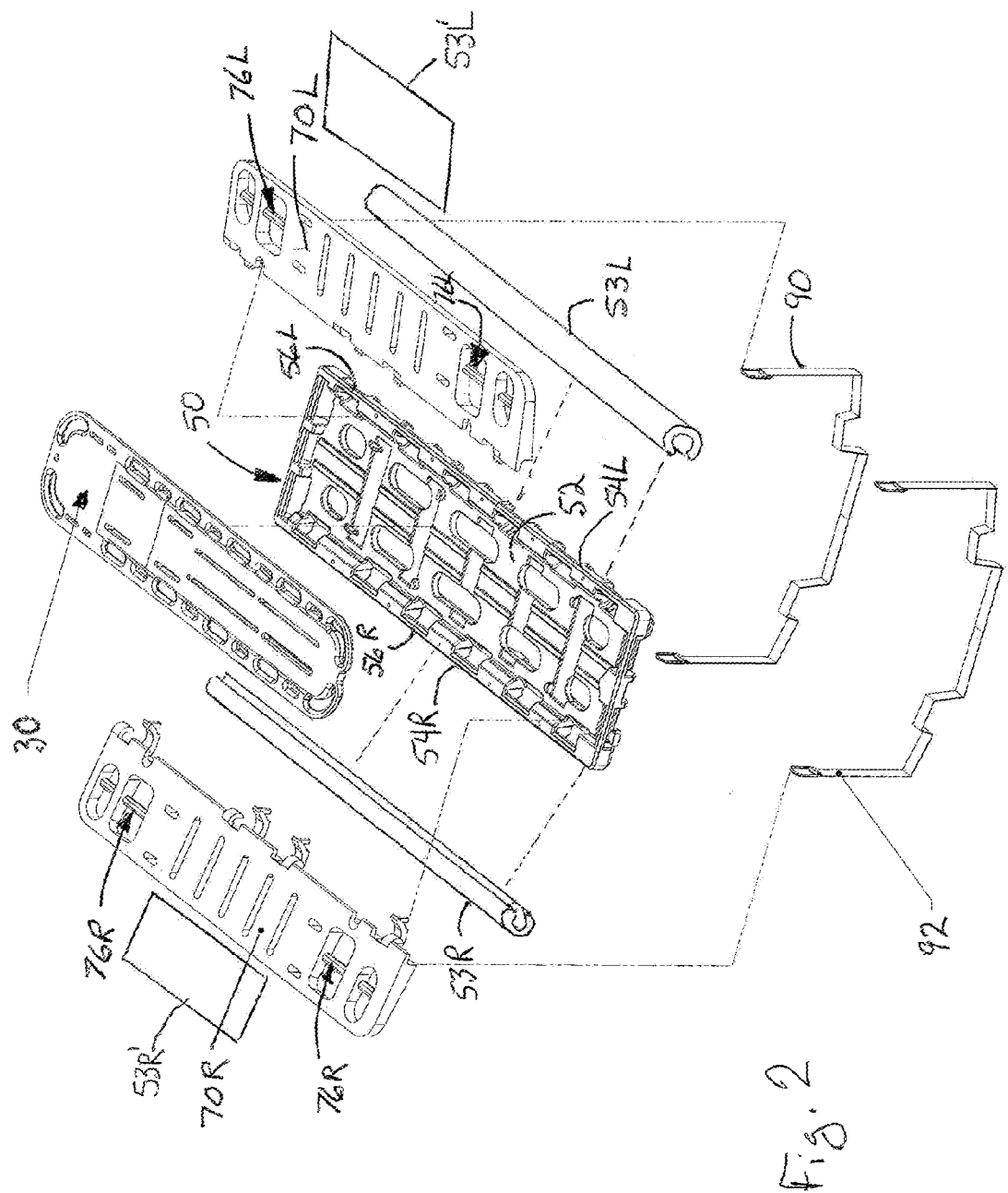
FIG. 2 is an exploded front perspective view of the first embodiment.

A first embodiment of the medical support surface of the present invention is depicted in FIGS. 1-3C generally at 20. As best seen in FIG. 2, medical support surface 20 includes rigid 15 backboard 30 defining an area capable of supporting a patient, support tray 50 having a recessed region 52 for receiving backboard 30, a set of two expander wings 70R and 70L attachable to lateral edges 54R and 54L respectively, of support tray 50. It is noted that expander wings 70R and 70L are optional features provided to accommodate larger patients and when used, will require the use of undergirding straps 90, 92 to facilitate lifting and carrying support surface 20. Further, the comfort 20 pads 53R and 53L normally secured to the lateral edges 54R and 54L, respectively, must be removed to afford access to the connecting rungs 56R and 56L extending there along in order to connect wings 70R and 70L. Equivalent pads 53R' and 53L' are placed on wings 70R and 70L for arm comfort.

As best seen in FIG. 1, backboard 30 is equipped with gel pad 40 for supporting the head and shoulders of a patient, gel pad 42 for supporting the patient's sacrum, and optionally, gel pad 44 may be provided at the foot of the backboard 30 to support a patient's heels. Gel pads 40, 42, and 44 are of the type described and claimed in U.S. patent application Ser. No. 11/715,101 filed Mar. 7, 2007 hereby incorporated by reference. Pads 40, 42, 44 are constructed of four-way stretch material, preferably made from elastane fibers. The chamber created thereby is filled with a medical grade gel, for example, gel sold under the trademark ISOGEL by Pittsburgh Plastics Manufacturing, Inc. of Butler, Pa. Tests run on gel pads made in accordance with the dictates of the present invention demonstrate a contact pressure below the pressure which has been determined to cause venous stasis, namely 26 mm of Mercury (0.50 psi). This is important when long-term contact is contemplated, as when a patient will remain on the board 30 from the time s/he is removed from the trauma site through all phases of diagnosis. A typical board without such gel pads tend to produce pressure sores leading care givers to quickly remove a patient from such a support surface risking the additional spinal injuries noted earlier. The reason the foot pads 44 are optional is that the feet do not remain immobilized as the head/shoulder region and sacrum do and are typically not as prone to experiencing pressure sores.

Each of the expander wings 70R and 70L have a plurality of upwardly extending hooks 72 and a plurality of downwardly extending hooks 74 which engage over octagonal rungs 56R and 56L along lateral edges 54R and 54L respectively. Rungs 56R and 56L are octagonal to facilitate clamping of various medical equipment thereto. As best seen in FIG. 3C, upwardly extending hook 72 is equipped with a tang 75 that is received in a recess 55 in tray 50 to secure wings 70R and 70L in place. As can be seen in FIG. 1, wings 70R and 70L are equipped with auxiliary rungs 76R and 76L having an octagonal cross section permitting clamping of the medical equipment when the expander wings are in use. Undergirding straps 90, 92 are woven through the wings 70R and 70L to enhance stability of the assembly.

Various changes, alternatives, and modifications will become apparent to a person of ordinary skill in the art after a reading of the foregoing specification. It is intended that all such changes, alternatives, and modifications as fall within the scope of the appended claims be considered part of the present invention.

I claim:

1. A medical support surface upon which a patient will lie for an extended period of time during transport from a trauma site in the medical emergency vehicle, through initial diagnosis and treatment until the patient is ready for her/his recovery bed, said medical support surface comprising:
   a) a radiologically transparent rigid backboard defining an area capable of supporting a patient, said backboard having a first pair of lateral edges;
   b) a radiologically transparent support tray having a recessed region for receiving said backboard upon which the patient lies;
   c) pressure relief pads attached to said rigid backboard, said pressure relief pads including
      i) four-way stretch urethane fabric forming an enclosure;
      ii) medical grade gel within said enclosure;
   said pressure relief pads configured to reduce a contact pressure between said backboard and a contacted portion of the patient's body to a pressure below that which causes venous stasis whereby the patient may remain on said rigid backboard for the extended period necessary for transport and treatment without causing skin ulcerations.

2. The medical support surface of claim 1 further comprising a set of expander wings attachable to lateral edges of said support tray to expand the area of said support surface beyond said first pair of lateral edges of said backboard.

3. The medical support surface of claim 2 wherein each of said wings is attachable to one of a second pair of lateral edges of said support tray by use of attachment means, said attachment means including a plurality of upwardly extending hooks and a plurality of downwardly extending hooks which cooperate to attach to rails extending along each of said second pair of lateral edges.

4. The medical support surface of claim 3 further comprising a plurality of tangs on said wings which are received in a plurality of recesses in said support tray to maintain said wings in a fixed longitudinal position relative thereto.

5. The medical support surface of claim 2 further comprising a pair of foam comfort 10 pads attached to said second pair of lateral edges of said support tray, said comfort pads being removable to permit attachment of said wings.

6. A medical support surface upon which a patient will lie for an extended period of time during transport from a trauma site in the medical emergency vehicle, through initial diagnosis and treatment until the patient is ready for her/his recovery bed, said medical support surface comprising:
   a) a radiologically transparent rigid backboard defining an area capable of supporting a patient, said backboard having a first pair of lateral edges;
   b) a radiologically transparent support tray having a recessed region for receiving said backboard upon which the patient lies;
   c) a plurality of expander wings, each of said wings including attachment means for securing said wing to one of a plurality of a second pair lateral edges of said support tray, said attachment means including
      i) a first plurality of upwardly extending hooks;
      ii) a second plurality of downwardly extending hooks, whereby said first and second pluralities of hooks cooperate to secure one of said expander wings along one of said lateral edges to expand an available surface area for supporting the patient;
   d) gel pads attached to said support surface and configured to reduce a contact pressure between said gel pads and a portion of a patient's anatomy to a level below 26 mm of Mercury (0.50 psi) to prevent venous stasis.

7. The medical support surface of claim 6 further comprising a plurality of tangs on said wings which are received in a plurality of recesses in said support tray to maintain said wings in a fixed longitudinal position relative thereto.

8. The medical support surface of claim 6 wherein said gel pads comprise a four-way stretch urethane fabric enclosure which encases a medical grade gel and cooperate with said gel to achieve the contact pressure below 26 mm of mercury.

* * * * *